US008372949B2

(12) United States Patent
Belcher

(10) Patent No.: US 8,372,949 B2
(45) Date of Patent: Feb. 12, 2013

(54) MOLECULAR RECOGNITION OF MATERIALS

(75) Inventor: Angela M. Belcher, Lexington, MA (US)

(73) Assignee: The Board of Regents, The University of Texas System, Austin, TX (US)

( * ) Notice: Subject to any disclaimer, the term of this patent is extended or adjusted under 35 U.S.C. 154(b) by 471 days.

(21) Appl. No.: 11/782,038

(22) Filed: Jul. 24, 2007

(65) Prior Publication Data

US 2008/0242552 A1 Oct. 2, 2008

Related U.S. Application Data

(63) Continuation of application No. 10/155,883, filed on May 24, 2002, now abandoned.

(60) Provisional application No. 60/296,013, filed on Jun. 5, 2001.

(51) Int. Cl.
*C07K 5/00* (2006.01)
*C40B 30/04* (2006.01)

(52) U.S. Cl. ............... 530/327; 530/321; 435/320.1; 506/14; 506/18; 506/21; 506/22

(58) Field of Classification Search .............. 530/327, 530/321; 435/320.1; 506/14, 18, 21, 22
See application file for complete search history.

(56) References Cited

U.S. PATENT DOCUMENTS

| | | | |
|---|---|---|---|
| 4,593,002 A | 6/1986 | Dulbecco | |
| 4,623,621 A | 11/1986 | Pestka | |
| 5,223,409 A | 6/1993 | Ladner et al. | |
| 5,264,563 A | 11/1993 | Huse | |
| 5,270,170 A | 12/1993 | Schatz et al. | |
| 5,316,922 A | 5/1994 | Brown et al. | |
| 5,403,484 A | 4/1995 | Ladner et al. | |
| 5,510,240 A | 4/1996 | Lam et al. | |
| 5,571,698 A | 11/1996 | Ladner et al. | |
| 5,585,646 A | 12/1996 | Kossovsky et al. | |
| 5,683,867 A | 11/1997 | Biesecker et al. | |
| 5,714,330 A | 2/1998 | Brenner et al. | |
| 5,723,323 A | 3/1998 | Kauffman et al. | |
| 5,739,305 A | 4/1998 | Cubicciotti | |
| 5,750,373 A | 5/1998 | Garrard et al. | |
| 5,751,018 A | 5/1998 | Alivisatos et al. | |
| 5,763,192 A | 6/1998 | Kauffman et al. | |
| 5,814,476 A | 9/1998 | Kauffman et al. | |
| 5,817,483 A | 10/1998 | Kauffman et al. | |
| 5,821,047 A | 10/1998 | Garrard et al. | |
| 5,824,514 A | 10/1998 | Kauffman et al. | |
| 5,837,500 A | 11/1998 | Ladner et al. | |
| 5,859,210 A | 1/1999 | Stowolitz et al. | |
| 5,864,013 A | 1/1999 | Goldberg | |
| 5,866,363 A | 2/1999 | Pieczenik | |
| 5,866,434 A | 2/1999 | Massey et al. | |
| 5,985,353 A | 11/1999 | Lawton et al. | |
| 5,990,479 A | 11/1999 | Weiss et al. | |
| 6,040,136 A | 3/2000 | Garrard et al. | |
| 6,100,035 A | 8/2000 | Kauffman et al. | |
| 6,114,038 A | 9/2000 | Castro et al. | |
| 6,207,392 B1 | 3/2001 | Weiss et al. | |
| 6,235,540 B1 | 5/2001 | Siiman et al. | |
| 6,413,723 B1 | 7/2002 | Kauffman et al. | |
| 6,417,340 B1 | 7/2002 | Mirkin et al. | |
| 6,423,538 B1 | 7/2002 | Wittrup et al. | |
| 6,472,147 B1 | 10/2002 | Janda et al. | |
| 6,492,107 B1 | 12/2002 | Kauffman et al. | |
| 6,569,641 B1 | 5/2003 | Kauffman et al. | |
| 6,593,137 B1 | 7/2003 | Erlanger et al. | |
| 7,470,379 B2 * | 12/2008 | Anderson et al. ....... 252/301.6 S |
| 2002/0114987 A1 | 8/2002 | Oscarsson et al. | |
| 2003/0068900 A1 | 4/2003 | Belcher | |
| 2003/0073104 A1 | 4/2003 | Belcher | |
| 2003/0113714 A1 | 6/2003 | Belcher | |
| 2003/0148380 A1 | 8/2003 | Belcher | |
| 2004/0018587 A1 * | 1/2004 | Makowski et al. .......... 435/68.1 |
| 2004/0127640 A1 | 7/2004 | Belcher et al. | |
| 2004/0197892 A1 | 10/2004 | Moore et al. | |
| 2005/0064508 A1 | 3/2005 | Belcher et al. | |

FOREIGN PATENT DOCUMENTS

| | | |
|---|---|---|
| EP | 0 552 267 B1 | 7/1993 |
| WO | WO 91/14696 | 10/1991 |
| WO | WO 99/13313 | 3/1999 |
| WO | WO 02/48701 A2 | 6/2002 |
| WO | WO 03/078451 | 9/2003 |

OTHER PUBLICATIONS

Aizenberg et al. (Apr. 8, 1999). "Control of crystal nucleation by patterned self-assembled monolayers." Nature 398:495-498.
Aizenberg et al. (Aug. 23, 2001) "Calcitic microlenses as part of the photoreceptor system in brittlestars." Nature, vol. 412: 819-822.
Alivisatos (1996). "Perspectives on the physical chemistry of semiconductor nanocrystals." J. Phys. Chem. B vol. 100, No. 31: 13226-13239.
Alivisatos (Aug. 4, 2000). "Naturally Aligned Nanocrystals" Science vol. 289, No. 5480: 736-737.
Alivisatos et al. (Aug. 15, 1996). "Organization of 'nanocrystal molecules' using DNA." Nature 382(6592):609-611.
Belcher et al. (May 2, 1996). "Control of crystal phase switching and orientation by soluble mollusk-shell proteins." Nature vol. 381 (No. 6577): 56-58.
Brown S. (Feb. 11, 2001). "Protein-mediated particle assembly." Amer. Chem. Soc. 1(7):391-394.
Brown S. (Mar. 15, 1997). "Metal-recognition by repeating polypeptides." Nature Biotechnology 15(3):269-272.
Brown, S. (1992). "Engineered Iron Oxide-Adhesion Mutants of the *Escherichia coli* phage lambda Receptor" Proceedings National Academy Sciences, USA, pp. 8651-8655.
Brown, Stanley, "Engineered iron oxide-adhesion mutants of the *Escherichia coli* phage λ receptor," Proc. Natl. Acad. Sci. USA, vol. 89, pp. 8651-8655 (1992).

(Continued)

*Primary Examiner* — Teresa Wessendorf
(74) *Attorney, Agent, or Firm* — Foley & Lardner LLP

(57) ABSTRACT

The present invention includes methods for selective binding of inorganic materials and the compositions that made up of the selecting agent and the target materials. One form of the present invention is a method for selecting crystal-binding peptides with binding specificity including the steps of contacting one or more amino acid oligomers with one or more single-crystals of a semiconductor material so that the oligomers may bind to the crystal and eluting the bound amino acid oligomers from the single-crystals.

8 Claims, 8 Drawing Sheets

OTHER PUBLICATIONS

Brown, Stanley, "Metal-recognition by repeating polypeptides," Nature Biotechnology, vol. 15, pp. 269-272 (1997).

Bruchez Jr. et al. (Sep. 25, 1998). "Semiconductor nanocrystals as fluorescent biological labels." Science 281:2013-2016.

Brummer et al., "Design, synthesis and characterization of panning agents for the selection of metalloantibodies," Letters in Peptide Science 6:395-302 (1999).

Budai et al. (Nov. 27, 1997). "Controlling the size, structure and orientation of semiconductor nanocrystals using metastable phase recrystallization." Nature vol. 390:384-386.

Cha et al. (Jan. 1999). "Silicatein filaments and subunits from a marine sponge direct the polymerization of silica and silicones in vitro." Proc. Natl. Acad. Sci., USA, vol. 96(2): 361-5.

Cha et al. (Jan. 20, 2000). "Biomimetic synthesis of ordered silica structures mediated by block copolypeptides." Nature 403:289-292.

Chalony et al. (Feb. 18, 1994). "The OZF gene encodes a protein consisting essentially of zinc finger motifs." J. Mol. Biol. 236:399-404.

Chen et al., "Noncovalent Sidewall Functionalization of Single-Walled Carbon Nanotubes for Protein Immobilization," Apr. 25, 2001, JACS, 123(16), pp. 3838-3839.

Collection of 62 slides and poster materials described further in the accompanying IDS and Belcher Declaration filed herewith.

Colvin et al. (Aug. 4, 1994). "Light-emitting diodes made from cadmium selenide nanocrystals and a semiconducting polymer." Nature 370:354-357.

Colvin et al., "Semiconductor nanocrystals covalently bound to metal surfaces with self-assembled monolayers," J. Am. Chem. Soc., vol. 114, pp. 5221-5230 (1992).

Dabbousi et al. (1997). "(CdSe)ZnS Core-Shell Quantum Dots: Synthesis and Optical and Structural, Characterization of a Size Series of Highly Luminescent Nanocrystallites." J. Phys. Chem. B, vol. 101(46): 9463-9475.

Dabbousi et al. (Mar. 13, 1995). "Electroluminescence of CdSe quantum-dot/polymer composites." Appl. Phys. Lett. 66(11):1316-1318.

Dameron et al., "Biosynthesis of cadmium sulphide quantum semiconductor crystallites," Nature, Apr. 13, 1989, vol. 338, pp. 596-597.

Davis et al., "The immobilization of proteins in carbon nanotubes," May 1, 1998, Inorganica Chimica Acta, vol. 272, Issues 1-2, pp. 261-266.

Efros et al. (2000). "The Electronic Structure of Semiconductor Nanocrystals," Annu. Rev. Mater. Sci. 30: 475-521.

El Yazal et al. (Sep. 18, 1999). "Ab Initio Calculations of Proton Dissociation Energies of Zinc Ligands: Hypothesis of Imidazolate as Zinc Ligand in Proteins." J. Phys. Chem. B 103:8773-8779.

Enshell-Seijffers et al. (2001). "The rational design of a 'type 88' genetically stable peptide display vector in the filamentous bacteriophage fd." Nucleic Acids Research 29(10):1-13.

Falini et al., "Control of Aragonite or Calcite Polymorphism by Mollusk Shell macromolecules," Science, vol. 271, pp. 67-69 (1996).

Field et al. (Sep. 21, 1998). "Ordering nanometer-scale magnets using bacterial thread templates." Appl. Phy. Lett. 73(12): 1739-1741.

Flynn et al. (Aug. 27, 2003) "Synthesis and Organization of Nanoscale II-VI Semiconductor Materials Using Evolved Peptide Specificity and Viral Capsid Assembly"; J. Mater. Sci., 13, 2414-2421.

Fritz et al. (Sep. 1, 1994). "Flat Pearls from biofabrication of organized composites on inorganic substrates." Nature, 371: 49-51.

Granja et al., "Channel-Mediated Transport of Glucose Across Lipid Bilayers," 1994, JACS, 116(23), pp. 10785-10786.

Green, A (1998). "Alteration of zif268 zinc-finger motifs gives rise to non-native zinc-co-ordination sites but preserves wild-type DNA recognition." Biochem. J., 333: 85-90.

Greenham et al. (Dec. 15, 1996). "Charge separation and transport in conjugated-polymer/semiconductor-nanocrystal composites studied by photoluminescence quenching and photoconductivity." The Amer. Phy. Soc. 54(24):17628-17637.

Grom et al. (Sep. 21, 2000). "Ordering and self-organization in nanocrystalline silicon." Nature 407: 358-361.

Gudiksen et al. (Feb. 7, 2002). "Growth of nanowire superlattice structures for nanoscale photonics and electronics." Nature 415:617-620.

Hall et al. (Feb. 16, 2001). "Site-specific organization of gold nanoparticles by biomolecular templating." ChemPhysChem, No. 3: 184-186.

Hartgerink et al. (Nov. 23, 2001). "Self-assembly and mineralization of peptide-amphiphile nanofibers." Science 294:1684-1688.

Hartgerink et al., "Peptide Nanotubes and Beyond," 1998, Chem. Eur. J., 4(8), pp. 1367-1372.

Heath et al. (1998). "Covalency in semiconductor quantum dots." Chemical Society Reviews vol. 27: 65-71.

Holmes et al. (Aug. 31, 1999). "Synthesis of Cadmium Sulfide Q Particles in Water-in-CO2 Microemulsions." Langmuir 15: 6613-6615.

Hori et al. (Jul. 29, 2000). "Artificial Zinc Finger Peptide Containing a Novel His4 Domain." J. Am. Chem. Soc. 122: 7648-7653.

Iannolo et al. (1995). "Modifying filamentous phage capsid: limits in the size of the major capsid protein." J. Mol. Biol. 248(4): 835-844.

Kanazawa et al. (Jun. 1, 1998). "Optical properties of PbS." J. Appl. Phys. vol. 83(No. 11): 5997-6001.

Kang et al. (Jul. 1997). "Electronic structure and optical properties of PbS and PbSe quantum dots." Journal of the Optical Society of America B:Optical Physics 14(7): 1632-1646.

Kellenberger et al. (1982). "The wrapping phenomenon in air-dried and negatively stained preparations." Ultramicroscopy 9:139-150.

Kim et al., "Organization of inorganic nanoparticles using biotin-streptavidin connectors," Chem. Mater., vol. 11, pp. 23-26 (1999).

Kishchenko et al. (1994). "Structure of a foreign peptide displayed on the surface of bacteriophage M13." J. Mol. Biol. 241(2): 208-13.

Klein et al. (Oct. 16, 1997). "A single-electron transistor made from a cadmium selenide nanocrystal." Nature 389:699-701.

Krebber et al. (1997). "Reliable cloning of functional antibody variable domains from hybridomas and spleen cell repertoires employing a reengineered phage display system." J. Immunol. Methods 201(1): 35-55.

Labrenz et al. (Dec. 1, 2000). "Formation of sphalerite (ZnS) deposits in natural biofilms of sulfate-reducing bacteria." Science 290(5497):1744-1747.

Lee et al. (2003). "Chiral smectic C structures of virus-based films." Langmuir 19(5):1592-1598.

Lee et al. (May 2, 2003). "Virus-based alignment of inorganic, organic, and biological nanosized materials." Adv. Mater. 15(9):689-692.

Lee et al. (May 3, 2002). "Ordering of quantum dots using genetically engineered viruses." Science 296(5569): 892-895.

Li et al. (Nov. 25, 1999). "Coupled synthesis and self-assembly of nanoparticles to give structures with controlled organization." Nature 402(6760): 393-395.

Mahtab et al. (1995). "Protein-Sized Quantum Dot Luminescence Can Distinguish between "Straight", "Bent", and "Kinked" Oligonucleotides." Journal of the American Chemical Society, 117(35): 9099-9100.

Mahtab et al. (1996). "Preferential Adsorption of a "Kinked" DNA to a Neutral Curved Surface: Comparisons to and Implications for Non-specific DNA-Protein Interactions." J. Am. Chem. Soc. 118(30): 7028-7032.

Malik et al. (1996). "New vectors for peptide display on the surface of filamentous bacteriophage." Gene 171: 49-51.

Malik et al. (2001). "Air-Stable Single-Source Precursors for the Synthesis of Chalcogenide Semiconductor Nanoparticles." Chem. Mater., 13: 913-920.

Malik et al. (Feb. 15, 1997). "Simultaneous display of different peptides on the surface of filamentous bacteriophage." Nucleic Acids Research 25(4):915-916.

Mann (2000). "The chemistry of form." Angew. Chem., Int. Ed. 39(19): 3393-3406.

Mann et al. (Sep. 3, 1993). "Crystallization at Inorganic-Organic Interfaces: Biominerals and Biomimetic Synthesis." Science 261: 1286-1292.

Mann, S. (Mar. 10, 1988). "Molecular recognition in biomineralization." Nature 332:119-124.

Mao et al. (Jun. 10, 2003). "Viral Assembly of Oriented Quantum Dot Nanowires"; PNAS, vol. 100, No. 12, pp. 6946-6951.

Mattoussi et al. (2000). "Self-Assembly of CdSe-ZnS Quantum Dot Bioconjugates Using an Engineered Recombinant Protein," Journal of the American Chemical Society 122(49): 12142-12150.

Mejare et al., "Selection of cadmium specific hexapeptides and their expression as OmpA fusion proteins in *Escherichia coli*," Protein Engineering 11(6):489-94 (1998).

Meldrum et al., "Electron microscopy study of magnetosomes in two cultured vibrioid magnetotactic bacteria," Proc. R. Soc. Lond. B, vol. 251, pp. 237-242 (1993).

Mely et al. (1996). "Zinc Binding to the HIV-1 Nucleocapsid Protein: A Thermodynamic Investigation by Fluorescence Spectroscopy." Biochemistry 35: 5175-5182.

Mirkin et al., "A DNA-based method for rationally assembling nanoparticles into macroscopic materials," Nature, vol. 382, pp. 607-609 (1996).

Muljarov et al. (Sep. 15, 2000). "Dielectrically enhanced excitons in semiconductor-insulator quantum wires: Theory and experiment." Physical Review B 62(11):7420-7432.

Murray et al. (1993). "Synthesis and Characterization of Nearly Monodisperse CdE (E=S,Se, Te) Semiconductor Nanocrystallites." J. Am. Chem. Soc. 115: 8706-8715.

Murray et al. (2000). "Synthesis and Characterization of Monodisperse Nanocrystals and Close-Packed Nanocrystal Assemblies," Annu. Rev. Mater. Sci. 30: 545-610.

Nanda et al. (2000), "Size-Selected Zinc Sulfide Nanocrystallites: Synthesis, Structure, and Optical Studies". Chem. Mater. 12: 1018-1024.

Parmley et al., "Antibody-selectable filamentous fd phage vectors: affinity purification of target genes," Gene, vol. 73, No. 2, pp. 305-318 (1988).

Peng et al. (Mar. 2, 2000). "Shape control of CdSe nanocrystals." Nature 404: 59-61.

Quinlan et al. (2000). "Reverse Micelle Synthesis and Characterization of ZnSe Nanoparticles." Langmuir 16(8): 4049-4051.

Reiss et al. (Jun. 6, 2002). "Highly Luminescent CdSe/ZnSe Core/Shell Nanocrystals of Low Size Dispersion." Nano Letters 2(7): 781-784.

Ricolleau et al. (1996). "Correlation between structural and optical properties of PbS nanocrystals." J. Cryst. Growth 166(1-4): 769-773.

Sannes-Lowery et al. (2000). "Measuring Dissociation Constants of RNA and Aminoglycoside Antibiotics by Electrospray Ionization Mass Spectrometry." Analytical Biochemistry 280: 264-271.

Sarkar et al. (Mar. 1975). "The morphology of murine oncornaviruses following different methods of preparation for electron microscopy." Cancer Research 35:740-749.

Schlamp et al. (Dec. 1, 1997). "Improved efficiencies in light emitting diodes made with CdSe(CdS) core/shell type nanocrystals and a semiconducting polymer." J. Appl. Phys. 82(11):5837-5842.

Scott et al., "Searching for Peptide Ligands with an Epitope Library," 1990, Science, 249 (4967), pp. 386-390.

Seeman (Apr. 30, 2002). "Emulating Biology: Building nanostructures from the bottom up." PNAS 99(2): 6451-6455.

Service, R.F., (1999), "Building the small world of the future", Science, 286; pp. 2442-2444.

Shenton et al. ((1999). "Inorganic-organic nanotube composites from template mineralization of tobacco mosaic virus." Adv. Mater. 11(3):253-256.

Shenton et al. (2001). "Synthesis of nanophase iron oxide in lumazine synthase capsids." Angew. Chem., Int. Ed. 40(2): 442-445.

Shenton et al. (Oct. 9, 1997). "Synthesis of cadmium sulfide superlattices using self-assembled bacterial S-layers." Nature 389(665 1): 585-587.

Symposium G., (1999), "Nonlithographic approaches to micro-and nanoscale organization", Nat. Science foundation, Session G1 (Abstract).

Tanaka et al. (Jun. 15, 2000). "Luminescence properties of ZnS phosphor nanocrystals prepared by the laser-induced gas-evaporation method." Journal of Applied Physics 87(12): 8535-8540.

Torres-Martinez et al. (1999). "Biomolecularly capped uniformly sized nanocrystalline materials: glutathione-capped ZnS nanocrystals." Nanotechnology 10(3): 340-354.

Vogel et al. (1997). "Sphalerite-Wurtzite Intermediates in Nanocrystalline CdS." Langmuir 13(4): 827-832.

Vossmeyer et al. (1994). "CdS Nanoclusters: Synthesis, Characterization, Size Dependent Oscillator Strength, Temperature Shift of the Excitonic Transition Energy, and Reversible Absorbance Shift." J. Phys. Chem. 98(31): 7665-7673.

Voyles et al. (Apr. 25, 2002). "Atomic-scale imaging of individual dopant atoms and clusters in highly n-type bulk Si." Nature 416:826-828.

Wang et al. (2001). "A novel and simple one-step solid-state reaction for the synthesis of PbS nanoparticles in the presence of a suitable surfactant." Materials Research Bulletin 36(11): 1977-1984.

Wang et al. (Aug. 24, 2001). "Highly polarized photoluminescence and photodetection from single indium phosphide nanowires." Science 293:1455-1457.

Weiner et al. (1997). "Design strategies in mineralized biological materials." Journal of Materials Chemistry 7(5): 689-702.

Weiner et al. (2000). "Materials design in biology." Materials Science & Engineering. C: Biomimetic and Supramolecular Systems C 11(1): 1-8.

Weiner, S. (1998). "The material bone: structure-mechanical function relations." Annual Review of Materials Science 28: 271-298.

Weller, H. (Jul. 3, 1998). "Transistor and light emitters from single nanoclusters." Angew. Chem. Int. Ed. 37(12):1658-1661.

Whaley et al. (Jun. 8, 2000). "Selection of peptides with semiconductor binding specificity for directed nanocrystal assembly." Nature, 405(6787): 665-668.

Whaley et al., "Borrowing Ideas from Nature: Peptide Specific Binding to Gallium Arsenide," Mat. Res. Soc. Symp. Proc., vol. 599, 2000, pp. 189-199.

Whitling et al., "A Combinatorial and Informatics Approach to CdS Nanoclusters," Adv. Mater., Sep. 15, 2000, vol. 12, No. 18, pp. 1377-1380.

Wu et al. (2002). "Block-by-block growth of single-crystalline Si/SiGe Superlattice nanowires." Nano. Lett, 2(2):83-86.

Yeh et al. (May 15, 1992). "Predictions and systematizations of the zincblende-wurtzite structural energies in binary octet compounds." Phys. Rev. B 45:12130-12133.

Zhang et al. (May 7, 2000). "Bacterial templating of zeolite fibres with hierarchical structure." Chem. Commun. 781-782.

Zwick et al. (Jan. 14, 2000). "Homodimeric peptides displayed by the major coat protein of filamentous phage." J. Mol. Biol. 300:307-320.

Dogic et al., "Smectic Phase in a Colloidal Suspension of Semiflexible Virus Particles," Physical Review Letters, Mar. 24, 1997, 78(12):2417-2420.

Dogic et al., "Cholesteric Phase in Virus Suspensions," Langmuir, 2000, 16:7820-7824.

Fowler et al., "Tobacco Mosaic Virus Liquid Crystals as Templates for the Interior Design of Silica Mesophases and Nanoparticles," Adv. Mater., Aug. 16, 2001, 13(16):1266-1269.

Dameron et al., "Characterization of Peptide-Coated Cadmium-Sulfide Crystallites," Inorg. Chem., 1990, 29:1343-1348.

\* cited by examiner

```
G13-5      A  M  A  G  T  T  S  D  P  S  T  V              SEQ ID NO.: 1
G12-5      P  A  Q  S  M  S  Q  T  P  S  A  A              SEQ ID NO.: 2
G12-3      H  T  H  T  N  N  D  S  P  N  Q  A              SEQ ID NO.: 3
G1-4                   D  T  Q  G  F  H  S  R  S  S  S  A  SEQ ID NO.: 4
G12-4               T  S  S  S  A  L  Q  P  A  H  A  W     SEQ ID NO.: 5
G14-3                  S  E  S  S  P  I  S  L  D  Y  R  A  SEQ ID NO.: 6
G7-4          S  T  H  N  Y  Q  I  P  R  P  P  T           SEQ ID NO.: 7
G15-5            H  P  F  S  N  E  P  L  Q  L  S  S        SEQ ID NO.: 8
G14-4      S  S  L  F  I  Q  Q  N  A  L  T  G              SEQ ID NO.: 9
G11-3         G  P  F  P  T  M  P  L  P  N  G  H           SEQ ID NO.: 10
G1-3          G  S  G  Q  L  P  I  A  L  E  L  R           SEQ ID NO.: 11
```

Fig. 1

CdS Single Crystal
12-mer library (N to C terminus)

| ID | # | 1 | 2 | 3 | 4 | 5 | 6 | 7 | 8 | 9 | 10 | SEQ ID |
|---|---|---|---|---|---|---|---|---|---|---|---|---|
| CEF-81 | E1 | C | H | A | S | N | R | L | S | C | | SEQ ID NO.:12 |
| CEF-82 | E2 | C | H | A | S | N | R | L | S | C | | SEQ ID NO.:12 |
| CEF-83 | E3 | C | H | A | S | N | R | L | S | C | | SEQ ID NO.:12 |
| CEF-84 | E4 | C | H | A | S | N | R | L | S | C | | SEQ ID NO.:12 |
| CEF-85 | E5 | C | H | A | S | N | R | L | S | C | | SEQ ID NO.:12 |
| CEF-86 | E6 | C | H | A | S | N | R | L | S | C | | SEQ ID NO.:12 |
| CEF-88 | E8 | C | H | A | S | N | R | L | S | C | | SEQ ID NO.:12 |
| CEF-89 | E9 | C | H | A | S | N | R | L | S | C | | SEQ ID NO.:12 |
| CEF-90 | E10 | C | H | A | S | N | R | L | S | C | | SEQ ID NO.:12 |
| CEF-91 | E11 | C | H | A | S | N | R | L | S | C | | SEQ ID NO.:12 |
| CEF-92 | E12 | C | H | A | S | N | R | L | S | C | | SEQ ID NO.:12 |
| CEF-159 | E13 | S | M | D | R | S | D | M | T | M | R | L | P | SEQ ID NO.:13 |
| CEF-160 | E14 | G | T | F | T | P | R | P | T | P | I | Y | P | SEQ ID NO.:14 |
| CEF-161 | E15 | Q | M | S | E | N | L | T | S | Q | I | E | S | SEQ ID NO.:15 |
| CEF-162 | E16 | D | M | L | A | R | L | R | A | T | A | G | P | SEQ ID NO.:16 |
| CEF-163 | E18 | S | Q | T | W | L | L | M | S | P | V | A | T | SEQ ID NO.:17 |
| CEF-164 | E19 | A | S | P | D | Q | Q | V | G | P | L | Y | V | SEQ ID NO.:18 |
| CEF-165 | E20 | L | T | W | S | P | L | Q | T | V | A | R | F | SEQ ID NO.:19 |
| CEF-166 | E21 | Q | I | S | A | H | Q | M | P | S | R | P | I | SEQ ID NO.:20 |
| CEF-167 | E22 | S | M | K | Y | N | L | I | V | D | S | P | Y | SEQ ID NO.:21 |
| CEF-168 | E23 | wt | | | | | | | | | | | | |
| CEF-169 | E24 | Q | M | P | I | R | N | Q | L | A | W | P | M | SEQ ID NO.:22 |
| CEF-170 | E25 | T | Q | N | L | E | I | R | E | P | L | T | P | SEQ ID NO.:23 |
| CEF-171 | E26 | Q | I | S | A | H | Q | M | P | S | R | P | I | SEQ ID NO.:20 |
| CEF-172 | E27 | Y | P | M | S | P | S | P | Y | P | Y | Q | L | SEQ ID NO.:24 |
| CEF-173 | E28 | S | F | M | I | Q | P | T | P | L | P | P | S | SEQ ID NO.:25 |
| CEF-174 | E29 | G | L | A | P | H | I | H | S | L | N | E | A | SEQ ID NO.:26 |
| CEF-175 | E30 | M | Q | F | P | V | T | P | Y | L | N | A | S | SEQ ID NO.:27 |

Fig. 4

CdS Biopan 3 Sequences (N to C terminus)

| | | | | | | | | | | | | |
|---|---|---|---|---|---|---|---|---|---|---|---|---|
| JCW-96  | S | P | G | D | S | L | K | K | L | A | A | S | SEQ ID NO.:28 |
| JCW-97  | S | P | G | D | S | L | K | K | L | A | A | S | SEQ ID NO.:28 |
| JCW-98  | Q | I | S | A | H | Q | M | P | S | R | P | I | SEQ ID NO.:20 |
| JCW-99  | S | P | G | D | S | L | K | K | L | A | A | S | SEQ ID NO.:28 |
| JCW-100 | S | P | G | D | S | L | K | K | L | A | A | S | SEQ ID NO.:28 |
| JCW-101 | S | P | G | D | S | L | K | K | L | A | A | S | SEQ ID NO.:28 |
| JCW-102 | S | P | G | D | S | L | K | K | L | A | A | S | SEQ ID NO.:28 |
| JCW-103 | S | P | G | D | S | L | K | K | L | A | A | S | SEQ ID NO.:28 |
| JCW-104 | S | P | G | D | S | L | K | K | L | A | A | S | SEQ ID NO.:28 |
| JCW-105 | G | Y | H | M | Q | T | L | P | G | P | V | A | SEQ ID NO.:29 |

CdS Biopan 4 Sequences (N to C terminus)

| | | | | | | | | | | | | |
|---|---|---|---|---|---|---|---|---|---|---|---|---|
| JCW-106 | S | L | T | P | L | T | T | S | H | L | R | S | SEQ ID NO.:30 |
| JCW-108 | S | L | T | P | L | T | T | S | H | L | R | S | SEQ ID NO.:30 |
| JCW-111 | S | L | T | P | L | T | T | S | H | L | R | S | SEQ ID NO.:30 |

CdS Biopan 5 Sequences (N to C terminus)

| | | | | | | | | | | | | |
|---|---|---|---|---|---|---|---|---|---|---|---|---|
| JCW-118 | T | L | T | N | G | P | L | R | P | F | T | G | SEQ ID NO.:31 |
| JCW-122 | S | L | T | P | L | T | T | S | H | L | R | S | SEQ ID NO.:30 |

CdS Biopan 3 Sequences (repeat; N to C terminus))

| | | | | | | | | | | | | |
|---|---|---|---|---|---|---|---|---|---|---|---|---|
| JCW-125 | S | P | G | D | S | L | K | K | L | A | A | S | SEQ ID NO.:28 |
| JCW-126 | S | P | G | D | S | L | K | K | L | A | A | S | SEQ ID NO.:28 |
| JCW-127 | S | P | G | D | S | L | K | K | L | A | A | S | SEQ ID NO.:28 |
| JCW-128 | S | P | G | D | S | L | K | K | L | A | A | S | SEQ ID NO.:28 |
| JCW-129 | S | P | G | D | S | L | K | K | L | A | A | S | SEQ ID NO.:28 |
| JCW-130 | S | L | T | P | L | T | T | S | H | L | R | S | SEQ ID NO.:30 |
| JCW-131 | S | P | G | D | S | L | K | K | L | A | A | S | SEQ ID NO.:28 |
| JCW-132 | WT | | | | | | | | | | | | |
| JCW-133 | S | P | G | D | S | L | K | K | L | A | A | S | SEQ ID NO.:28 |
| JCW-134 | S | P | G | D | S | L | K | K | L | A | A | S | SEQ ID NO.:28 |

CdS Biopan 2 Sequences (N to C terminus)

| | | | | | | | | | | | | |
|---|---|---|---|---|---|---|---|---|---|---|---|---|
| JCW-137 | S | L | T | P | L | T | T | S | H | L | R | S | SEQ ID NO.:30 |
| JCW-139 | S | L | T | P | L | T | T | S | H | L | R | S | SEQ ID NO.:30 |
| JCW-140 | S | L | T | P | L | T | T | S | H | L | R | S | SEQ ID NO.:30 |
| JCW-141 | S | L | T | P | L | T | T | S | H | L | R | S | SEQ ID NO.:30 |

CdS Biopan 5 Sequences (repeat; N to C terminus)

| | | | | | | | | | | | | |
|---|---|---|---|---|---|---|---|---|---|---|---|---|
| JCW-146 | T | L | T | N | G | P | L | R | P | F | T | G | SEQ ID NO.:31 |
| JCW-148 | L | N | T | P | K | P | F | T | L | G | Q | N | SEQ ID NO.:32 |

Fig. 5

Other arrangements (N to C terminus)

| | | | | | | | | | | | |
|---|---|---|---|---|---|---|---|---|---|---|---|
| 4 | B71 | CEF-215 | C | D | L | Q | N | Y | K | A | C | SEQ ID NO.:33 |
| 4 | G | CEF-156 | C | R | H | P | H | T | R | L | C | SEQ ID NO.:34 |
| 3t | H13 | CEF-131 | C | A | N | L | K | P | K | A | C | SEQ ID NO.:35 |
| 3t | H15 | CEF-133 | C | Y | I | N | P | P | K | V | C | SEQ ID NO.:36 |
| 3t | H14 | CEF-132 | C | N | N | K | V | P | V | L | C | SEQ ID NO.:37 |
| 3 | B49 | CEF-203 | C | H | A | S | K | T | P | L | C | SEQ ID NO.:38 |
| 3t | H2 | CEF-120 | C | A | S | Q | L | Y | P | A | C | SEQ ID NO.:39 |
| 3 | G4 | CEF-102 | C | N | M | T | Q | Y | P | A | C | SEQ ID NO.:40 |
| 3t | H17 | CEF-135 | C | F | A | P | S | G | P | A | C | SEQ ID NO.:41 |
| 4 | | B20 | C | P | V | W | I | Q | A | P | C | SEQ ID NO.:42 |
| 5 | CEF-27 | B29 | C | Q | V | A | V | N | P | L | C | SEQ ID NO.:43 |
| 3 | G2 | CEF-100 | C | Q | P | E | A | M | P | A | C | SEQ ID NO.:44 |
| 3 | B48 | CEF-202 | C | H | P | T | M | P | L | A | C | SEQ ID NO.:45 |
| 3a | B92 | CEF-229 | C | P | P | F | A | A | P | I | C | SEQ ID NO.:46 | his-met-pro sequences from Aldrich ZnS screenings

| | | | | | | | | | | | |
|---|---|---|---|---|---|---|---|---|---|---|---|
| 3a | B63 | CEF-207 | C | N | K | H | Q | P | M | H | C | SEQ ID NO.:47 |
| 4 | | B18 | C | F | P | M | R | S | N | Q | C | SEQ ID NO.:48 |
| 4a | B73 | CEF-217 | C | Q | S | M | P | H | N | R | C | SEQ ID NO.:49 |
| 5 | | B7 | C | N | N | P | M | H | Q | N | C | SEQ ID NO.:50 |
| 5 | CEF-28 | B30 | C | Q | S | M | P | H | N | R | C | SEQ ID NO.:49 |
| 5 | CEF-34 | B36 | C | H | M | A | P | R | W | Q | C | SEQ ID NO.:51 |
| 5 | CEF-35 | B37 | C | Q | S | M | P | H | N | R | C | SEQ ID NO.:49 |
| | JCW-87 | 503 | H | V | H | I | H | S | R | P | M | SEQ ID NO.:52 |
| | JCW-87 | 503 | H | V | H | I | H | S | R | P | M | SEQ ID NO.:52 |
| 5 | JCW-65 | 5H7 | L | P | N | M | H | P | L | P | L | SEQ ID NO.:53 |
| 4 | JCW-57 | 4H9 | L | P | L | R | L | P | P | M | P | SEQ ID NO.:54 |
| 4 | JCW-30 | 437-10 | H | S | M | I | G | T | P | T | T | SEQ ID NO.:55 |
| 4 | JCW-28 | 437-8 | S | V | S | V | G | M | K | P | S | SEQ ID NO.:56 |
| 4 | JCW-21 | 437-1 | L | D | A | S | F | M | Q | D | W | SEQ ID NO.:57 |
| 4 | JCW-22 | 437-2 | T | P | P | S | Y | Q | M | A | M | SEQ ID NO.:58 |
| 4 | JCW-23 | 437-3 | Y | P | Q | L | V | S | M | S | T | SEQ ID NO.:59 |
| 3 | JCW-3 | 337-3 | G | Y | S | T | I | N | M | Y | S | SEQ ID NO.:60 |
| 5 | CEF-11 | Z35 | S | V | S | V | G | M | K | P | S | SEQ ID NO.:56 |
| 5 | CEF-6 | Z30 | D | R | M | L | L | P | F | N | L | SEQ ID NO.:61 |
| 5 | CEF-3 | Z27 | I | P | M | T | P | S | Y | D | S | SEQ ID NO.:62 |
| 5 | | Z22 | M | Y | S | P | R | P | P | A | L | SEQ ID NO.:63 |
| 5 | | Z23 | Q | P | T | T | D | L | M | A | H | SEQ ID NO.:64 |
| 5 | | Z15 | A | T | H | V | Q | M | A | W | A | SEQ ID NO.:65 |
| 5 | | Z9 | S | M | H | A | T | L | T | P | M | SEQ ID NO.:66 |
| 5 | | Z10 | S | G | P | A | H | G | M | F | A | SEQ ID NO.:67 |
| 2 | | Z4 | I | A | N | R | P | Y | S | A | Q | SEQ ID NO.:68 |
| | | C16 | V | M | T | Q | P | T | R | | | SEQ ID NO.:69 |
| | | C10 | H | M | R | P | L | S | I | | | SEQ ID NO.:70 |

Fig. 6

| | | | | | | | | | | | | | |
|---|---|---|---|---|---|---|---|---|---|---|---|---|---|
| ZnS capping: | | BP5 | | | | | | | | | | | |
| | | Z6 | L | T | R | S | P | L | H | V | D | Q | R | R | SEQ ID NO.:71 |
| | | Z8 | V | I | S | N | H | A | E | S | S | R | R | L | SEQ ID NO.:72 |
| | | Z10 | S | G | P | A | H | G | M | F | A | R | P | L | SEQ ID NO.:67 |
| ZnS 12-mer repeats | | | | | | | | | | | | | | |
| 5 | JCW-44 | 537-4 | S | V | S | V | G | M | K | P | S | P | R | P | SEQ ID NO.:56 |
| 4 | JCW-28 | 437-8 | S | V | S | V | G | M | K | P | S | P | R | P | SEQ ID NO.:56 |
| 5 | CEF-11 | Z35 | S | V | S | V | G | M | K | P | S | P | R | P | SEQ ID NO.:56 |
| CdS contamination | | | | | | | | | | | | | | |
| 1 | CEF-83 | E3 | C | H | A | S | N | R | L | S | C | | | | SEQ ID NO.: 12 |
| PbS 7-mer repeats 7C | | | | | | | | | | | | | | |
| 4a | JCW-72 | P74-4 | H | T | H | I | P | N | Q | | | | | | SEQ ID NO.:73 |
| 4 | JCW-74 | P74-6 | H | T | H | I | P | N | Q | | | | | | SEQ ID NO.:73 |
| 5 | JCW-76 | P75-2 | L | A | P | V | S | P | P | | | | | | SEQ ID NO.:74 |
| 5 | JCW-78 | P75-4 | L | A | P | V | S | P | P | | | | | | SEQ ID NO.:74 |
| 7C repeats | | | | | | | | | | | | | | |
| | B73 | CEF-217 | C | Q | S | M | P | H | N | R | C | | | | SEQ ID NO.:49 |
| 5 | CEF-35 | B37 | C | Q | S | M | P | H | N | R | C | | | | SEQ ID NO.:49 |
| 5 | CEF-28 | B30 | C | Q | S | M | P | H | N | R | C | | | | SEQ ID NO.:49 |
| 3t | G5 | CEF-103 | C | M | T | A | G | K | N | T | C | | | | SEQ ID NO.:75 |
| 3t | G7 | CEF-105 | C | Q | T | L | W | R | N | S | C | | | | SEQ ID NO.:76 |
| 3a | B93 | CEF-230 | C | T | S | V | H | T | N | T | C | | | | SEQ ID NO.:77 |
| 5 | CEF-30 | B32 | C | T | S | V | H | T | N | T | C | | | | SEQ ID NO.:77 |
| 4a | B72 | CEF-216 | C | P | S | L | A | M | N | S | C | | | | SEQ ID NO.:78 |
| 5 | CEF-23 | B25 | C | P | S | L | A | M | N | S | C | | | | SEQ ID NO.:78 |
| 5 | CEF-33 | B35 | C | S | N | N | T | V | H | A | C | | | | SEQ ID NO.:79 |
| 5 | CEF-25 | B27 | C | S | N | N | T | V | H | A | C | | | | SEQ ID NO.:79 |
| 5 | CEF-37 | B39 | C | L | P | A | Q | G | H | V | C | | | | SEQ ID NO.:80 |
| 5 | CEF-29 | B31 | C | L | P | A | Q | V | H | V | C | | | | SEQ ID NO.:81 |
| 5 | CEF-22 | B24 | C | L | P | A | Q | G | H | V | C | | | | SEQ ID NO.:80 |
| 3a | B96 | CEF-234 | C | P | P | K | N | V | R | L | C | | | | SEQ ID NO.:82 |
| 4 | G | CEF-158 | C | P | H | I | N | A | H | A | C | | | | SEQ ID NO.:83 |
| 4 | G | CEF-149 | C | I | V | N | L | A | R | A | C | | | | SEQ ID NO.:84 |

Fig. 7

Biopan 4 Lead Sulfide

| | | | | | | | | | | | | |
|---|---|---|---|---|---|---|---|---|---|---|---|---|
| JCW-154 | T | M | G | F | T | A | P | R | F | P | H | Y | SEQ ID NO.:85 |
| JCW-155 | A | T | Q | S | Y | V | R | H | P | S | L | G | SEQ ID NO.:86 |
| JCW-156 | T | S | T | T | Q | G | A | L | A | Y | L | F | SEQ ID NO.:87 |
| JCW-157 | D | P | P | W | S | A | I | V | R | H | R | D | SEQ ID NO.:88 |
| JCW-158 | F | D | N | K | P | F | L | R | V | A | S | E | SEQ ID NO.:89 |
| JCW-159 | H | Q | S | H | T | Q | Q | N | K | R | H | L | SEQ ID NO.:90 |
| JCW-160 | T | S | T | T | Q | G | A | L | A | Y | L | F | SEQ ID NO.:91 |
| JCW-161 | K | T | P | I | H | T | S | A | W | E | F | Q | SEQ ID NO.:92 |
| JCW-162 | D | P | P | W | S | A | I | V | R | H | R | D | SEQ ID NO.:88 |
| JCW-163 | T | M | G | F | T | A | P | R | F | R | H | Y | SEQ ID NO.:85 |

Biopan 5 Lead Sulfide

| | | | | | | | | | | | | |
|---|---|---|---|---|---|---|---|---|---|---|---|---|
| JCW-164 | T | M | G | F | T | A | P | R | F | P | H | Y | SEQ ID NO.:85 |
| JCW-165 | T | M | G | F | T | A | P | R | F | P | H | Y | SEQ ID NO.:85 |
| JCW-166 | D | L | F | H | L | K | P | V | S | N | E | K | SEQ ID NO.:93 |
| JCW-167 | T | M | G | F | T | A | P | R | F | P | H | Y | SEQ ID NO.:85 |
| JCW-168 | D | P | P | W | S | A | I | V | R | H | R | D | SEQ ID NO.:88 |
| JCW-169 | K | P | F | W | T | S | S | P | D | V | M | T | SEQ ID NO.:94 |
| JCW-170 | D | P | P | W | S | A | I | V | R | H | R | D | SEQ ID NO.:88 |
| JCW-171 | P | W | A | A | T | S | K | P | P | Y | S | S | SEQ ID NO.:95 |
| JCW-172 | T | M | G | F | T | A | P | R | F | P | H | Y | SEQ ID NO.:85 |
| JCW-173 | T | M | G | F | T | A | P | R | F | P | H | Y | SEQ ID NO.:85 |

Fig. 8

MOLECULAR RECOGNITION OF MATERIALS

CROSS REFERENCE TO RELATED APPLICATIONS

This application is a Continuation of application Ser. No. 10/155,883, filed May 24, 2002, which claims priority to Provisional Patent Application No. 60/296,013, filed Jun. 5, 2001, the contents of both of which are incorporated herein by reference in their entirety.

The research carried out in the subject application was supported in part by a grant from the Army Research Office (Grant No. DADD19-99-0155). The U.S. government has certain rights in this invention.

FIELD OF THE INVENTION

The present invention is directed to the selective recognition of inorganic materials in general and specifically toward surface recognition of single crystals of semiconductor and magnetic materials using small organic molecules.

BACKGROUND OF THE INVENTION

In biological systems, organic molecules exert a remarkable level of control over the nucleation and mineral phase of inorganic materials such as calcium carbonate and silica, and over the assembly of crystallites and other nanoscale building blocks into complex structures required for biological function.

Materials produced by biological processes are typically soft, and consist of a surprisingly simple collection of molecular building blocks (i.e., lipids, peptides, and nucleic acids) arranged in astoundingly complex architectures. Unlike the semiconductor industry, which relies on a serial lithographic processing approach for constructing the smallest features on an integrated circuit, living organisms execute their architectural "blueprints" using mostly non-covalent forces acting simultaneously upon many molecular components. Furthermore, these structures can often elegantly rearrange between two or more usable forms without changing any of the molecular constituents.

The use of "biological" materials to process the next generation of microelectronic devices provides a possible solution to resolving the limitations of traditional processing methods. The critical factors in this approach are identifying the appropriate compatibilities and combinations of biological-inorganic materials, and the synthesis of the appropriate building blocks.

SUMMARY OF THE INVENTION

The ability to direct the assembly of nanoscale components into controlled and sophisticated structures has motivated intense efforts to develop assembly methods that mimic or exploit the recognition capabilities and interactions found in biological systems. Of particular value would be methods that could be applied to materials with interesting electronic or optical properties, but natural evolution has not selected for interactions between biomolecules and such materials.

The present invention is based on recognition that biological systems efficiently and accurately assemble nanoscale building blocks into complex and functionally sophisticated structures with high perfection, controlled size and compositional uniformity.

The present invention includes methods for selective binding of inorganic materials and the compositions that are made up of the selecting agent and the target materials. One form of the present invention is a method for selecting crystal-binding peptides with binding specificity and includes the steps of contacting one or more amino acid oligomers with one or more single-crystals of a semiconductor material so that the oligomers may bind to the crystal and eluting the bound amino acid oligomers from the single-crystals. Another form of the present invention is a method for selecting crystal-binding peptides with binding specificity and includes the steps of contacting one or more amino acid oligomers with one or more crystals of a semiconductor, such as a Group III-V or II-VI material; or a magnetic material, such an iron oxide, so that the oligomers may bind to the crystal and eluting the bound amino acid oligomers from the single-crystals.

Another form of the present invention is a peptide sequence for the binding GaAs (100) chosen from the group consisting of Seq. ID Nos. 1 through 11.

Still another form of the present invention is a method for selecting polymeric organic molecules, lipids or nucleic acids with binding specificity. A method of the present invention begins by contacting one or more oligomers with one or more single-crystals of a magnetic material so that the oligomers may bind to the crystal and eluting the bound peptide oligomers from the single-crystals. The sequence of the organic polymer is then determined by direct or indirect sequencing.

Another form of the present invention is a method for selecting crystal-bonding amino acids including the steps of contacting one or more amino acid oligomers with one or more crystals of a target material so that the oligomers may bind to the crystal and eluting the bound amino acid oligomers from the crystals.

Another form of the present invention is a specificity structure made up of one or more single crystals of gallium arsenide, indium phosphide, mercury cadmium telluride, zinc sulfide, cadmium sulfide, aluminum-gallium-arsenide, zinc selenide, cadmium selenide, cadmium telluride, zinc telluride, aluminum arsenide, indium arsenide and the like and a selective binding amino acid sequence.

Another form of the present invention is a crystal binding amino acid oligomer made up of the sequence motif (ser/tyr/thr)-(arg/asp/ser)-X-aa-(ser/asn/glu/arg/thr)-Xaa-Xaa-ser/thr/glu/asp)-(ser/thr/tyr) (SEQ. ID NO. 159) or Xaa-Xaa-(ser/tyr/thr)-(arg/asp/ser)-Xaa-(ser/asn/glu/arg/thr)-Xaa-Xaa-(ser/thr/glu/asp)-(ser/thr/tyr)-(ser/thr/his)-Xaa-Xaa (SEQ. ID NO 160).

The motifs and other polymers referred to in the descriptions of various embodiments of the present invention may be free molecules, e.g. amino acid oligomers, or they may be part of a chimera, such as a phage display.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1 depicts selected random amino acid sequences in accordance with the present invention.

FIGS. 4-8 depict specific amino acid sequences in accordance with the present invention.

DETAILED DESCRIPTION OF THE INVENTION

Figure 2A:
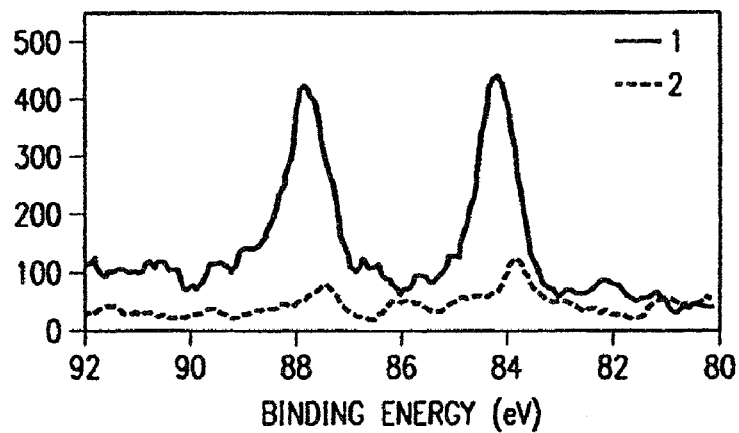
FIG. 2 depicts XPS spectra of structures in accordance with the present invention

Although making and using various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

The facility with which biological systems assemble immensely complicated structure on an exceedingly minute scale has motivated a great deal of interest in the desire to identify non-biological systems that can behave in a similar fashion. Of particular value would be methods that could be applied to materials with interesting electronic or optical properties, but natural evolution has not selected for interactions between biomolecules and such materials.

The present invention is based on recognition that biological systems efficiently and accurately assemble nanoscale building blocks into complex and functionally sophisticated structures with high perfection, controlled size and compositional uniformity.

One method of providing a random organic polymer pool is using a Phage-display library, based on a combinatorial library of random peptides containing between 7 and 12 amino acids fused to the pIII coat protein of M13 coliphage, provided different peptides that were reacted with crystalline semiconductor structures. Five copies of the pIII coat protein are located on one end of the phage particle, accounting for 10-16 nm of the particle. The phage-display approach provided a physical linkage between the peptide substrate interaction and the DNA that encodes that interaction. The examples described here used as examples, five different single-crystal semiconductors: GaAs(100), GaAs(111)A, GaAs(111)B, InP(100) and Si(100). These substrates allowed for systematic evaluation of the peptide substrate interactions and confirmation of the general utility of the methodology of the present invention for different crystalline structures.

Protein sequences that successfully bound to the specific crystal were eluted from the surface, amplified by, e.g., a million-fold, and reacted against the substrate under more stringent conditions. This procedure was repeated five times to select the phage in the library with the most specific binding. After, e.g., the third, fourth and fifth rounds of phage selection, crystal-specific phage were isolated and their DNA sequenced. Peptide binding has been identified that is selective for the crystal composition (for example, binding to GaAs but not to Si) and crystalline face (for example, binding to (100) GaAs, but not to (111)B GaAs).

Twenty clones selected from GaAs(100) were analyzed to determine epitope binding domains to the GaAs surface. The partial peptide sequences of the modified pIII or pVIII protein are shown in FIG. 1, revealing similar amino-acid sequences among peptides exposed to GaAs. With increasing number of exposures to a GaAs surface, the number of uncharged polar and Lewis-base functional groups increased. Phage clones from third, fourth and fifth round sequencing contained on average 30%, 40% and 44% polar functional groups, respectively, while the fraction of Lewis-base functional groups increased at the same time from 41% to 48% to 55%. The observed increase in Lewis bases, which should constitute only 34% of the functional groups in random 12-mer peptides from our library, suggests that interactions between Lewis bases on the peptides and Lewis-acid sites on the GaAs surface may mediate the selective binding exhibited by these clones.

The expected structure of the modified 12-mers selected from the library may be an extended conformation, which seems likely for small peptides, making the peptide much longer than the unit cell (5.65 A°) of GaAs. Therefore, only small binding domains would be necessary for the peptide to recognize a GaAs crystal. These short peptide domains, highlighted in FIG. 1, contain serine- and threonine-rich regions in addition to the presence of amine Lewis bases, such as asparagine and glutamine. To determine the exact binding sequence, the surfaces have been screened with shorter libraries, including 7-mer and disulphide constrained 7-mer libraries. Using these shorter libraries that reduce the size and flexibility of the binding domain, fewer peptide-surface interactions are allowed, yielding the expected increase in the strength of interactions between generations of selection.

Figure 2B:
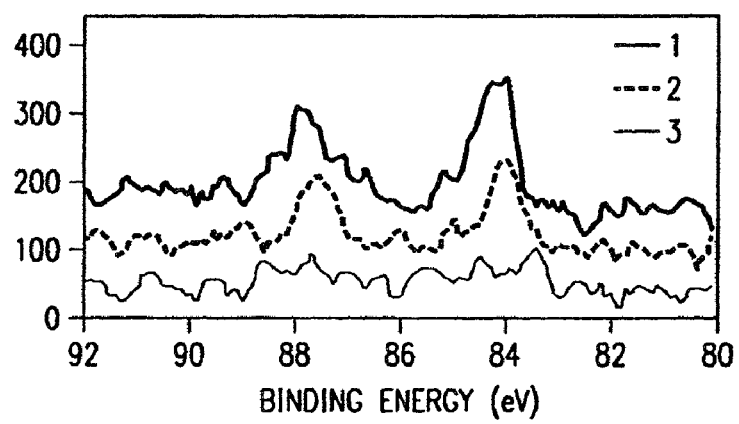
Figure 2C:
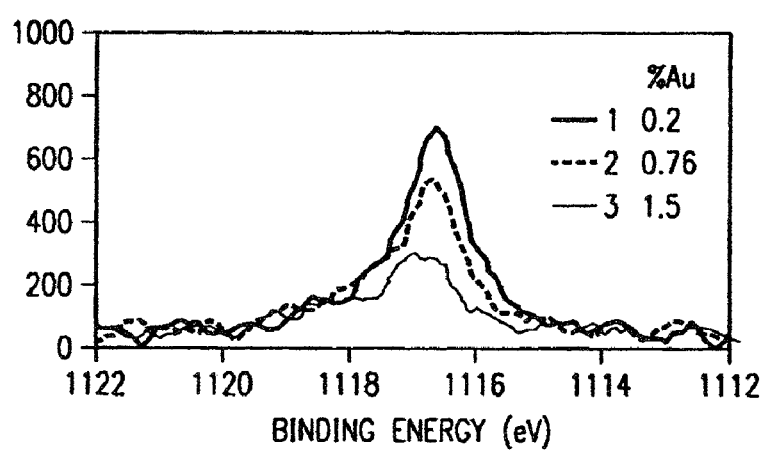

Phage, tagged with streptavidin-labelled 20-nm colloidal gold particles bound to the phage through a biotinylated antibody to the M13 coat protein, were used for quantitative assessment of specific binding. X-ray photoelectron spectroscopy (XPS) elemental composition determination was performed, monitoring the phage substrate interaction through the intensity of the gold 4f-electron signal (FIG. 2a-c). Without the presence of the G1-3 phage, the antibody and the gold streptavidin did not bind to the GaAs(100)substrate. The gold-streptavidin binding was, therefore, specific to the phage and an indicator of the phage binding to the substrate. Using XPS it was also found that the G1-3 clone isolated from GaAs(100) bound specifically to GaAs(100) but not to Si(100) (see FIG. 2a). In complementary fashion the S1 clone, screened against the (100) Si surface, showed poor binding to the (100) GaAs surface.

Some GaAs clones also bound the surface of InP (100), another zinc-blende structure. The basis of the selective binding, whether it is chemical, structural or electronic, is still under investigation. In addition, the presence of native oxide on the substrate surface may alter the selectivity of peptide binding.

The preferential binding of the G1-3 clone to GaAs(100), over the (111)A (gallium terminated) or (111)B (arsenic terminated) face of GaAs was demonstrated (FIG. 2b, c). The G1-3 clone surface concentration was greater on the (100) surface, which was used for its selection, than on the gallium-rich (111)A or arsenic-rich (111)B surfaces. These different surfaces are known to exhibit different chemical reactivities, and it is not surprising that there is selectivity demonstrated in the phage binding to the various crystal faces. Although the bulk termination of both 111 surfaces give the same geometric structure, the differences between having Ga or As atoms outermost in the surface bilayer become more apparent when comparing surface reconstructions. The composition of the oxides of the various GaAs surfaces is also expected to be different, and this in turn may affect the nature of the peptide binding.

The intensity of Ga 2 p electrons against the binding energy from substrates that were exposed to the G1-3 phage clone is plotted in 2c. As expected from the results in FIG. 2b, the Ga 2 p intensities observed on the GaAs (100), (111)A and (111)B surfaces are inversely proportional to the gold concentrations. The decrease in Ga 2 p intensity on surfaces with higher gold-streptavidin concentrations was due to the increase in surface coverage by the phage. XPS is a surface technique with a sampling depth of approximately 30 angstroms; therefore, as the thickness of the organic layer increases, the signal from the inorganic substrate decreases.

This observation was used to confirm that the intensity of gold-streptavidin was indeed due to the presence of phage containing a crystal specific bonding sequence on the surface of GaAs. Binding studies were performed that correlate with the XPS data, where equal numbers of specific phage clones were exposed to various semiconductor substrates with equal surface areas. Wild-type clones (no random peptide insert) did not bind to GaAs (no plaques were detected). For the G1-3 clone, the eluted phage population was 12 times greater from GaAs(100) than from the GaAs(111)A surface.

The G1-3, G12-3 and G7-4 clones bound to GaAs(100) and InP(100) were imaged using atomic force microscopy (AFM). The InP crystal has a zinc-blende structure, isostructural with GaAs, although the In—P bond has greater ionic character than the GaAs bond. The 10-nm width and 900-nm length of the observed phage in AFM matches the dimensions of the M13 phage observed by transmission electron microscopy (TEM), and the gold spheres bound to M13 antibodies were observed bound to the phage (data not shown). The InP surface has a high concentration of phage. These data suggest that there are many factors involved in substrate recognition, including atom size, charge, polarity and crystal structure.

The G1-3 clone (negatively stained) is seen bound to a GaAs crystalline wafer in the TEM image (not shown). The data confirms that binding was directed by the modified pIII protein of G1-3, not through non-specific interactions with the major coat protein. Therefore, peptides of the present invention may be used to direct specific peptide-semiconductor interactions in assembling nanostructures and heterostructures (FIG. 3e).

X-ray fluorescence microscopy was used to demonstrate the preferential attachment of phage to a zinc-blende surface in close proximity to a surface of differing chemical and structural composition. A nested square pattern was etched into a GaAs wafer; this pattern contained 1-µm lines of GaAs, and 4-µm $SiO_2$ spacings in between each line (FIGS. 3a, 3b). The G12-3 clones were interacted with the GaAs/$SiO_2$ patterned substrate, washed to reduce non-specific binding, and tagged with an immuno-fluorescent probe, tetramethyl rhodamine (TMR). The tagged phage were found as the three red lines and the center dot, in FIG. 3b, corresponding to G12-3 binding only to GaAs. The $SiO_2$ regions of the pattern remain unbound by phage and are dark in color. This result was not observed on a control that was not exposed to phage, but was exposed to the primary antibody and TMR (FIG. 3a). The same result was obtained using non-phage bound G12-3 peptide.

Figure 3:
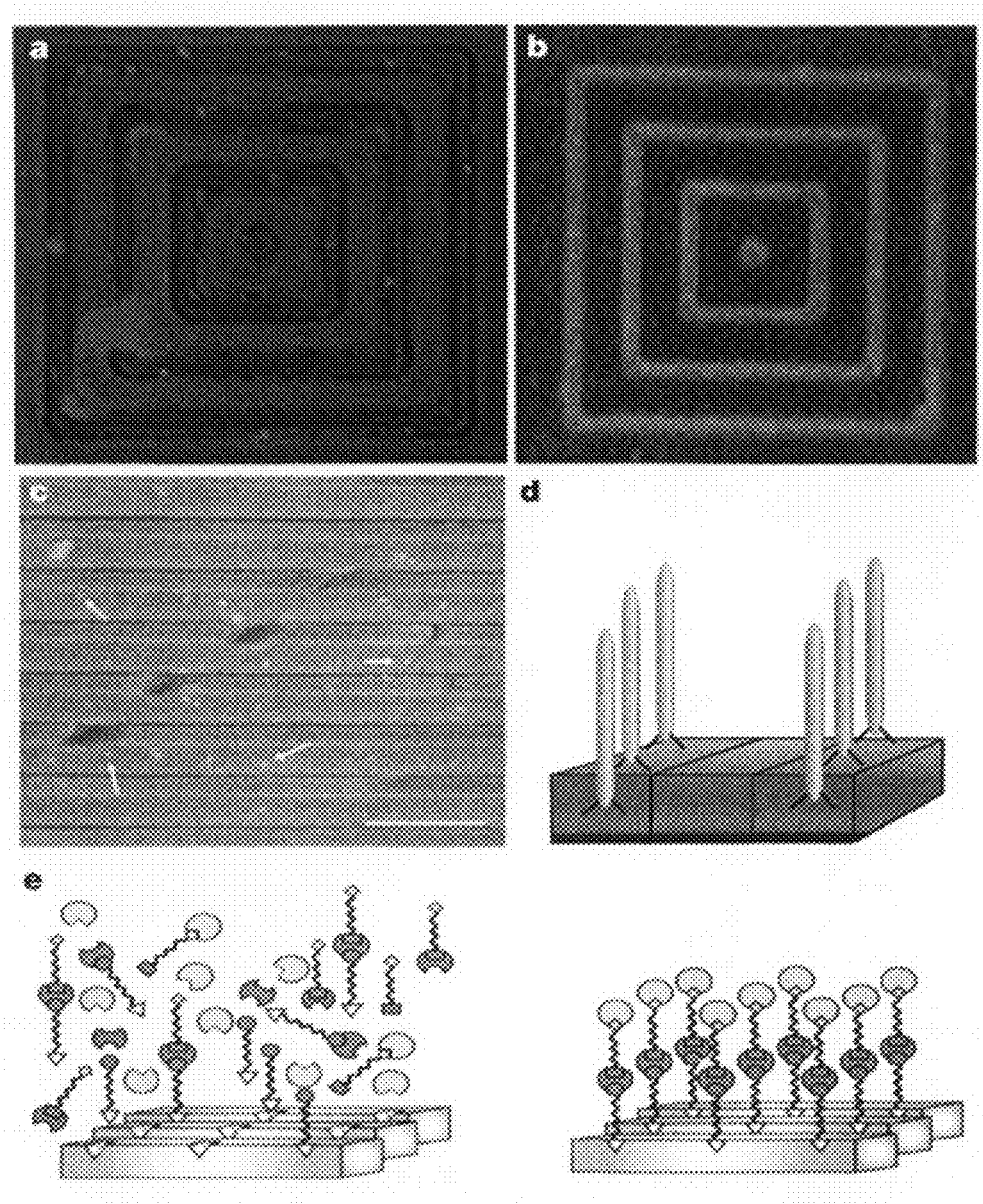
FIG. 3 depicts phage recognition of heterostructures in accordance with the present invention.

The GaAs clone G12-3 was observed to be substrate-specific for GaAs over AlGaAs (FIG. 3c). AlAs and GaAs have essentially identical lattice constraints at room temperature, 5.66 A° and 5.65 A°, respectively, and thus ternary alloys of AlxGa1-xAs can be epitaxially grown on GaAs substrates. GaAs and AlGaAs have zinc-blende crystal structures, but the G12-3 clone exhibited selectivity in binding only to GaAs. A multilayer substrate was used, consisting of alternating layers of GaAs and of $Al_{0.98}Ga_{0.02}As$. The substrate material was cleaved and subsequently reacted with the G12-3 clone.

The G12-3 clones were labeled with 20-nm gold-streptavidin nanoparticles. Examination by scanning electron microscopy (SEM) shows the alternating layers of GaAs and $Al_{0.98}Ga_{0.02}As$ within the heterostructure (FIG. 3c). X-ray elemental analysis of gallium and aluminum was used to map the gold-streptavidin particles exclusively to the GaAs layers of the heterostructure, demonstrating the high degree of binding specificity for chemical composition. In FIG. 3d, a model for the discrimination of phage for semiconductor heterostructures, as seen in the fluorescence and SEM images (FIGS. 3a-c).

The present invention demonstrates the power use of phage-display libraries to identify, develop and amplify binding between organic peptide sequences and inorganic semiconductor substrates. This peptide recognition and specificity of inorganic crystals has been extended to other substrates, including GaN, ZnS, CdS, $Fe_3O_4$, $Fe_2O_3$, CdSe, ZnSe and $CaCO_3$ using peptide libraries. Bivalent synthetic peptides with two-component recognition (FIG. 4e) are currently being designed; such peptides have the potential to direct nanoparticles to specific locations on a semiconductor structure. These organic and inorganic pairs should provide powerful building blocks for the fabrication of a new generation of complex, sophisticated electronic structures.

EXAMPLES

Peptide selection. The phage display or peptide library was contacted with the semiconductor, or other, crystals in Tris-buffered saline (TBS) containing 0.1% TWEEN-20, to reduce phage-phage interactions on the surface. After rocking for 1 h at room temperature, the surfaces were washed with 10 exposures to Tris-buffered saline, pH 7.5, and increasing TWEEN-20 concentrations from 0.1% to 0.5% (v/v). The phage were eluted from the surface by the addition of glycine-HCl (pH 2.2) 10 minute, transferred to a fresh tube and then neutralized with Tris-HCl (pH 9.1). The eluted phage were titred and binding efficiency was compared.

The phage eluted after third-round substrate exposure were mixed with their *Escherichia coli* ER2537 host and plated on LB XGal/IPTG plates. Since the library phage were derived from the vector M13mp19, which carries the laczA gene, phage plaques were blue in color when plated on media containing Xgal (5-bromo-4-chloro-3-indoyl-.beta.-D-galactoside) and IPTG (isopropyl-.beta.-D-thiogalactoside). Blue/white screening was used to select phage plaques with the random peptide insert. Plaques were picked and DNA sequenced from these plates.

Substrate preparation. Substrate orientations were confirmed by X-ray diffraction, and native oxides were removed by appropriate chemical specific etching. The following etches were tested on GaAs and InP surfaces: $NH_4OH:H_2O$ 1:10, $HCl:H_2O$ 1:10, $H_3PO_4:H_2O_2:H_2O$ 3:1:50 at 1 minute and 10 minute etch times. The best element ratio and least oxide formation (using XPS) for GaAs and InP etched surfaces was achieved using $HCl:H_2O$ for 1 minute followed by a deionized water rinse for 1 minute. However, since an ammonium hydroxide etch was used for GaAs in the initial screening of the library, this etch was used for all other GaAs substrate examples. Si(100) wafers were etched in a solution of $HF:H_2O$ 1:40 for one minute, followed by a deionized water rinse. All surfaces were taken directly from the rinse solution and immediately introduced to the phage library. Surfaces of control substrates, not exposed to phage, were characterized and mapped for effectiveness of the etching process and morphology of surfaces by AFM and XPS.

Multilayer substrates of GaAs and of $Al_{0.98}Ga_{0.02}$As were grown by molecular beam epitaxy onto (100) GaAs. The epitaxially grown layers were Si-doped (n-type) at a level of $5 \times 10^{-7}$ $cm^{-3}$.

Antibody and Gold Labeling. For the XPS, SEM and AFM examples, substrates were exposed to phage for 1 h in Tris-buffered saline then introduced to an anti-fd bacteriophage-biotin conjugate, an antibody to the pIII protein of fd phage, (1:500 in phosphate buffer, Sigma) for 30 minute and then rinsed in phosphate buffer. A streptavidin/20-nm colloidal gold label (1:200 in phosphate buffered saline (PBS), Sigma) was attached to the biotin-conjugated phage through a biotin-streptavidin interaction; the surfaces were exposed to the label for 30 minutes and then rinsed several times with PBS.

X-ray Photoelectron Spectroscopy (XPS). The following controls were done for the XPS examples to ensure that the gold signal seen in XPS was from gold bound to the phage and not non-specific antibody interaction with the GaAs surface. The prepared (100) GaAs surface was exposed to (1) antibody and the streptavidin-gold label, but without phage, (2) G1-3 phage and streptavidin-gold label, but without the antibody, and (3) streptavidin-gold label, without either G1-3 phage or antibody.

The XPS instrument used was a Physical Electronics Phi ESCA 5700 with an aluminum anode producing monochromatic 1,487-eV X-rays. All samples were introduced to the chamber immediately after gold-tagging the phage (as described above) to limit oxidation of the GaAs surfaces, and then pumped overnight at high vacuum to reduce sample outgassing in the XPS chamber.

Atomic Force Microscopy (AFM). The AFM used was a Digital Instruments Bioscope mounted on a Zeiss Axiovert 100s-2tv, operating in tip scanning mode with a G scanner. The images were taken in air using tapping mode. The AFM probes were etched silicon with 125-mm cantilevers and spring constants of 20.+−.100 Nm-1 driven near their resonant frequency of 200.+−0.400 kHz. Scan rates were of the order of 1.+−0.5 mms-1. Images were leveled using a first-order plane to remove sample tilt.

Transmission Electron Microscopy (TEM). TEM images were taken using a Philips EM208 at 60 kV. The G1-3 phage (diluted 1:100 in TBS) were incubated with GaAs pieces (500 mm) for 30 minute, centrifuged to separate particles from unbound phage, rinsed with TBS, and resuspended in TBS. Samples were stained with 2% uranyl acetate.

Scanning Electron Microscopy (SEM). The G12-3 phage (diluted 1:100 in TBS) were incubated with a freshly cleaved hetero-structure surface for 30 minute and rinsed with TBS. The G12-3 phage were tagged with 20-nm colloidal gold. SEM and elemental mapping images were collected using the Norian detection system mounted on a Hitachi 4700 field emission scanning electron microscope at 5 kV.

Although this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An isolated peptide sequence that selectively binds to a crystalline face of a target crystal, wherein the peptide sequence is selected from the group consisting of SEQ. ID. Nos. 1 to 11, which has been isolated from phage display library or a combinatorial library.

2. The isolated peptide sequence according to claim 1, wherein the target crystal is a single crystal.

3. The isolated peptide sequence according to claim 1, wherein the target crystal is an inorganic crystal.

4. The isolated peptide sequence according to claim 1, wherein the target crystal is a semiconductor crystal.

5. The isolated peptide sequence according to claim 1, wherein the target crystal is a Group III-V semiconductor crystal or a Group II-VI semiconductor crystal.

6. The isolated peptide sequence according to claim 1, wherein the target crystal is a nanoparticle.

7. The isolated peptide sequence according to claim 1, wherein the target crystal is gallium arsenide, indium phosphide, gallium nitride, zinc sulfide, cadmium sulfide, aluminum arsenide, gallium stibinide, aluminum gallium arsenide, aluminum stibinide, aluminum arsenide, cadmium selenide, zinc selenide, cadmium telluride, zinc selenide, indium arsenide, silicon, FePd, cobalt, manganese, lithium niobate, iron oxide, silica or calcium carbonate.

8. The composition according to claim 1, wherein the peptide binding sequence is bound to a nanoparticle, a surface, or a patterned surface.

* * * * *

```
                        SEQUENCE LISTING

<160> NUMBER OF SEQ ID NOS: 95

<210> SEQ ID NO 1
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 1

Ala Met Ala Gly Thr Thr Ser Asp Pro Ser Thr Val
1               5                   10

<210> SEQ ID NO 2
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 2

Ala Ala Ser Pro Thr Gln Ser Met Ser Gln Ala Pro
1               5                   10

<210> SEQ ID NO 3
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 3

His Thr His Thr Asn Asn Asp Ser Pro Asn Gln Ala
1               5                   10
```

```
<210> SEQ ID NO 4
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 4

Asp Thr Gln Gly Phe His Ser Arg Ser Ser Ser Ala
1               5                   10

<210> SEQ ID NO 5
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 5

Thr Ser Ser Ser Ala Leu Gln Pro Ala His Ala Trp
1               5                   10

<210> SEQ ID NO 6
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 6

Ser Glu Ser Ser Pro Ile Ser Leu Asp Tyr Arg Ala
1               5                   10

<210> SEQ ID NO 7
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 7

Ser Thr His Asn Tyr Gln Ile Pro Arg Pro Pro Thr
1               5                   10

<210> SEQ ID NO 8
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 8

His Pro Phe Ser Asn Glu Pro Leu Gln Leu Ser Ser
1               5                   10

<210> SEQ ID NO 9
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 9
```

```
Gly Thr Leu Ala Asn Gln Gln Ile Phe Leu Ser Ser
1               5                   10

<210> SEQ ID NO 10
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 10

His Gly Asn Pro Leu Pro Met Thr Pro Phe Pro Gly
1               5                   10

<210> SEQ ID NO 11
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 11

Arg Leu Glu Leu Ala Ile Pro Leu Gln Gly Ser Gly
1               5                   10

<210> SEQ ID NO 12
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 12

Cys His Ala Ser Asn Arg Leu Ser Cys
1               5

<210> SEQ ID NO 13
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 13

Ser Met Asp Arg Ser Asp Met Thr Met Arg Leu Pro
1               5                   10

<210> SEQ ID NO 14
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 14

Gly Thr Phe Thr Pro Arg Pro Thr Pro Ile Tyr Pro
1               5                   10

<210> SEQ ID NO 15
<211> LENGTH: 12
<212> TYPE: PRT
<213> ORGANISM: artificial sequence
<220> FEATURE:
<223> OTHER INFORMATION: peptide binding sequence retrieved from phage
```

-continued biopanning

<400> SEQUENCE: 15

Gln Met Ser Glu Asn Leu Thr Ser Gln Ile Glu Ser
1               5                   10

<210> SEQ ID NO 16
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 16

Asp Met Leu Ala Arg Leu Arg Ala Thr Ala Gly Pro
1               5                   10

<210> SEQ ID NO 17
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 17

Ser Gln Thr Trp Leu Leu Met Ser Pro Val Ala Thr
1               5                   10

<210> SEQ ID NO 18
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 18

Ala Ser Pro Asp Gln Gln Val Gly Pro Leu Tyr Val
1               5                   10

<210> SEQ ID NO 19
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 19

Leu Thr Trp Ser Pro Leu Gln Thr Val Ala Arg Phe
1               5                   10

<210> SEQ ID NO 20
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 20

Gln Ile Ser Ala His Gln Met Pro Ser Arg Pro Ile
1               5                   10

<210> SEQ ID NO 21
<211> LENGTH: 12

```
<212> TYPE: PRT
<213> ORGANISM: artificial sequence
<220> FEATURE:
<223> OTHER INFORMATION: peptide binding sequence retrieved from phage
      biopanning

<400> SEQUENCE: 21

Ser Met Lys Tyr Asn Leu Ile Val Asp Ser Pro Tyr
1               5                   10

<210> SEQ ID NO 22
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 22

Gln Met Pro Ile Arg Asn Gln Leu Ala Trp Pro Met
1               5                   10

<210> SEQ ID NO 23
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 23

Thr Gln Asn Leu Glu Ile Arg Glu Pro Leu Thr Pro
1               5                   10

<210> SEQ ID NO 24
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 24

Tyr Pro Met Ser Pro Ser Pro Tyr Pro Tyr Gln Leu
1               5                   10

<210> SEQ ID NO 25
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 25

Ser Phe Met Ile Gln Pro Thr Pro Leu Pro Pro Ser
1               5                   10

<210> SEQ ID NO 26
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 26

Gly Leu Ala Pro His Ile His Ser Leu Asn Glu Ala
1               5                   10
```

```
<210> SEQ ID NO 27
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 27

Met Gln Phe Pro Val Thr Pro Tyr Leu Asn Ala Ser
1               5                   10

<210> SEQ ID NO 28
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 28

Ser Pro Gly Asp Ser Leu Lys Lys Leu Ala Ala Ser
1               5                   10

<210> SEQ ID NO 29
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 29

Gly Tyr His Met Gln Thr Leu Pro Gly Pro Val Ala
1               5                   10

<210> SEQ ID NO 30
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 30

Ser Leu Thr Pro Leu Thr Thr Ser His Leu Arg Ser
1               5                   10

<210> SEQ ID NO 31
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 31

Thr Leu Thr Asn Gly Pro Leu Arg Pro Phe Thr Gly
1               5                   10

<210> SEQ ID NO 32
<211> LENGTH: 12
<212> TYPE: PRT
<213> ORGANISM: artificial sequence
<220> FEATURE:
<223> OTHER INFORMATION: peptide binding sequence retrieved from phage
      biopanning
```

```
<400> SEQUENCE: 32

Leu Asn Thr Pro Lys Pro Phe Thr Leu Gly Gln Asn
1               5                   10

<210> SEQ ID NO 33
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 33

Cys Asp Leu Gln Asn Tyr Lys Ala Cys
1               5

<210> SEQ ID NO 34
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 34

Cys Arg His Pro His Thr Arg Leu Cys
1               5

<210> SEQ ID NO 35
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 35

Cys Ala Asn Leu Lys Pro Lys Ala Cys
1               5

<210> SEQ ID NO 36
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 36

Cys Tyr Ile Asn Pro Pro Lys Val Cys
1               5

<210> SEQ ID NO 37
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 37

Cys Asn Asn Lys Val Pro Val Leu Cys
1               5

<210> SEQ ID NO 38
<211> LENGTH: 9
<212> TYPE: PRT
<213> ORGANISM: artificial sequence
```

```
<220> FEATURE:
<223> OTHER INFORMATION: peptide binding sequence retrieved from phage
      biopanning

<400> SEQUENCE: 38

Cys His Ala Ser Lys Thr Pro Leu Cys
1               5

<210> SEQ ID NO 39
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 39

Cys Ala Ser Gln Leu Tyr Pro Ala Cys
1               5

<210> SEQ ID NO 40
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 40

Cys Asn Met Thr Gln Tyr Pro Ala Cys
1               5

<210> SEQ ID NO 41
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 41

Cys Phe Ala Pro Ser Gly Pro Ala Cys
1               5

<210> SEQ ID NO 42
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 42

Cys Pro Val Trp Ile Gln Ala Pro Cys
1               5

<210> SEQ ID NO 43
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 43

Cys Gln Val Ala Val Asn Pro Leu Cys
1               5
```

```
<210> SEQ ID NO 44
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 44

Cys Gln Pro Glu Ala Met Pro Ala Cys
1               5

<210> SEQ ID NO 45
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 45

Cys His Pro Thr Met Pro Leu Ala Cys
1               5

<210> SEQ ID NO 46
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 46

Cys Pro Pro Phe Ala Ala Pro Ile Cys
1               5

<210> SEQ ID NO 47
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 47

Cys Asn Lys His Gln Pro Met His Cys
1               5

<210> SEQ ID NO 48
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 48

Cys Phe Pro Met Arg Ser Asn Gln Cys
1               5

<210> SEQ ID NO 49
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 49
```

Cys Gln Ser Met Pro His Asn Arg Cys
1               5

<210> SEQ ID NO 50
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 50

Cys Asn Asn Pro Met His Gln Asn Cys
1               5

<210> SEQ ID NO 51
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 51

Cys His Met Ala Pro Arg Trp Gln Cys
1               5

<210> SEQ ID NO 52
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 52

His Val His Ile His Ser Arg Pro Met
1               5

<210> SEQ ID NO 53
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 53

Leu Pro Asn Met His Pro Leu Pro Leu
1               5

<210> SEQ ID NO 54
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 54

Leu Pro Leu Arg Leu Pro Pro Met Pro
1               5

<210> SEQ ID NO 55
<211> LENGTH: 9
<212> TYPE: PRT
<213> ORGANISM: artificial sequence
<220> FEATURE:
<223> OTHER INFORMATION: peptide binding sequence retrieved from phage -continued

```
biopanning

<400> SEQUENCE: 55

His Ser Met Ile Gly Thr Pro Thr Thr
1               5

<210> SEQ ID NO 56
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 56

Ser Val Ser Val Gly Met Lys Pro Ser
1               5

<210> SEQ ID NO 57
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 57

Leu Asp Ala Ser Phe Met Gln Asp Trp
1               5

<210> SEQ ID NO 58
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 58

Thr Pro Pro Ser Tyr Gln Met Ala Met
1               5

<210> SEQ ID NO 59
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 59

Tyr Pro Gln Leu Val Ser Met Ser Thr
1               5

<210> SEQ ID NO 60
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 60

Gly Tyr Ser Thr Ile Asn Met Tyr Ser
1               5

<210> SEQ ID NO 61
<211> LENGTH: 9
```

```
<212> TYPE: PRT
<213> ORGANISM: artificial sequence
<220> FEATURE:
<223> OTHER INFORMATION: peptide binding sequence retrieved from phage
      biopanning

<400> SEQUENCE: 61

Asp Arg Met Leu Leu Pro Phe Asn Leu
1               5

<210> SEQ ID NO 62
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 62

Ile Pro Met Thr Pro Ser Tyr Asp Ser
1               5

<210> SEQ ID NO 63
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 63

Met Tyr Ser Pro Arg Pro Pro Ala Leu
1               5

<210> SEQ ID NO 64
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 64

Gln Pro Thr Thr Asp Leu Met Ala His
1               5

<210> SEQ ID NO 65
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 65

Ala Thr His Val Gln Met Ala Trp Ala
1               5

<210> SEQ ID NO 66
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 66

Ser Met His Ala Thr Leu Thr Pro Met
1               5
```

<210> SEQ ID NO 67
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 67

Ser Gly Pro Ala His Gly Met Phe Ala
1               5

<210> SEQ ID NO 68
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 68

Ile Ala Asn Arg Pro Tyr Ser Ala Gln
1               5

<210> SEQ ID NO 69
<211> LENGTH: 7
<212> TYPE: PRT
<213> ORGANISM: artificial sequence
<220> FEATURE:
<223> OTHER INFORMATION: peptide binding sequence retrieved from phage
      biopanning

<400> SEQUENCE: 69

Val Met Thr Gln Pro Thr Arg
1               5

<210> SEQ ID NO 70
<211> LENGTH: 7
<212> TYPE: PRT
<213> ORGANISM: artificial sequence
<220> FEATURE:
<223> OTHER INFORMATION: peptide binding sequence retrieved from phage
      biopanning

<400> SEQUENCE: 70

His Met Arg Pro Leu Ser Ile
1               5

<210> SEQ ID NO 71
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 71

Leu Thr Arg Ser Pro Leu His Val Asp Gln Arg Arg
1               5                   10

<210> SEQ ID NO 72
<211> LENGTH: 12
<212> TYPE: PRT
<213> ORGANISM: artificial sequence
<220> FEATURE:
<223> OTHER INFORMATION: peptide binding sequence retrieved from phage
      biopanning

```
<400> SEQUENCE: 72

Val Ile Ser Asn His Ala Glu Ser Ser Arg Arg Leu
1               5                   10

<210> SEQ ID NO 73
<211> LENGTH: 7
<212> TYPE: PRT
<213> ORGANISM: artificial sequence
<220> FEATURE:
<223> OTHER INFORMATION: peptide binding sequence retrieved from phage
      biopanning

<400> SEQUENCE: 73

His Thr His Ile Pro Asn Gln
1               5

<210> SEQ ID NO 74
<211> LENGTH: 7
<212> TYPE: PRT
<213> ORGANISM: artificial sequence
<220> FEATURE:
<223> OTHER INFORMATION: peptide binding sequence retrieved from phage
      biopanning

<400> SEQUENCE: 74

Leu Ala Pro Val Ser Pro Pro
1               5

<210> SEQ ID NO 75
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 75

Cys Met Thr Ala Gly Lys Asn Thr Cys
1               5

<210> SEQ ID NO 76
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 76

Cys Gln Thr Leu Trp Arg Asn Ser Cys
1               5

<210> SEQ ID NO 77
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 77

Cys Thr Ser Val His Thr Asn Thr Cys
1               5

<210> SEQ ID NO 78
<211> LENGTH: 9
<212> TYPE: PRT
<213> ORGANISM: artificial sequence
```

```
<220> FEATURE:
<223> OTHER INFORMATION: peptide binding sequence retrieved from phage
      biopanning

<400> SEQUENCE: 78

Cys Pro Ser Leu Ala Met Asn Ser Cys
1               5

<210> SEQ ID NO 79
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 79

Cys Ser Asn Asn Thr Val His Ala Cys
1               5

<210> SEQ ID NO 80
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 80

Cys Leu Pro Ala Gln Gly His Val Cys
1               5

<210> SEQ ID NO 81
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 81

Cys Leu Pro Ala Gln Val His Val Cys
1               5

<210> SEQ ID NO 82
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 82

Cys Pro Pro Lys Asn Val Arg Leu Cys
1               5

<210> SEQ ID NO 83
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 83

Cys Pro His Ile Asn Ala His Ala Cys
1               5
```

```
<210> SEQ ID NO 84
<211> LENGTH: 9
<212> TYPE: PRT
<213> ORGANISM: artificial sequence
<220> FEATURE:
<223> OTHER INFORMATION: peptide binding sequence retrieved from phage
      biopanning

<400> SEQUENCE: 84

Cys Ile Val Asn Leu Ala Arg Ala Cys
1               5

<210> SEQ ID NO 85
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 85

Thr Met Gly Phe Thr Ala Pro Arg Phe Pro His Tyr
1               5                   10

<210> SEQ ID NO 86
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 86

Ala Thr Gln Ser Tyr Val Arg His Pro Ser Leu Gly
1               5                   10

<210> SEQ ID NO 87
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 87

Thr Ser Thr Thr Gln Gly Ala Leu Ala Tyr Leu Phe
1               5                   10

<210> SEQ ID NO 88
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 88

Asp Pro Pro Trp Ser Ala Ile Val Arg His Arg Asp
1               5                   10

<210> SEQ ID NO 89
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 89
```

```
Phe Asp Asn Lys Pro Phe Leu Arg Val Ala Ser Glu
1               5                   10
```

<210> SEQ ID NO 90
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 90

```
His Gln Ser His Thr Gln Gln Asn Lys Arg His Leu
1               5                   10
```

<210> SEQ ID NO 91
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 91

```
Thr Ser Thr Thr Gln Gly Ala Leu Ala Tyr Leu Phe
1               5                   10
```

<210> SEQ ID NO 92
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 92

```
Lys Thr Pro Ile His Thr Ser Ala Trp Glu Phe Gln
1               5                   10
```

<210> SEQ ID NO 93
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 93

```
Asp Leu Phe His Leu Lys Pro Val Ser Asn Glu Lys
1               5                   10
```

<210> SEQ ID NO 94
<211> LENGTH: 12
<212> TYPE: PRT
<213> ORGANISM: artificial sequence
<220> FEATURE:
<223> OTHER INFORMATION: peptide binding sequence retrieved from phage
      biopanning

<400> SEQUENCE: 94

```
Lys Pro Phe Trp Thr Ser Ser Pro Asp Val Met Thr
1               5                   10
```

<210> SEQ ID NO 95
<211> LENGTH: 12
<212> TYPE: PRT
<213> ORGANISM: artificial sequence
<220> FEATURE:
<223> OTHER INFORMATION: peptide binding sequence retrieved from phage -continued biopanning

<400> SEQUENCE: 95

```
Pro Trp Ala Ala Thr Ser Lys Pro Pro Tyr Ser Ser
1               5                   10
```